United States Patent [19]
Lee

[11] Patent Number: 5,354,437
[45] Date of Patent: Oct. 11, 1994

[54] MULTI-ELEMENT MICROELECTROPOLISHING METHOD

[75] Inventor: Peter J. Lee, Middleton, Wis.

[73] Assignee: Wisconsin Alumni Research Foundation, Madison, Wis.

[21] Appl. No.: 107,241

[22] Filed: Aug. 16, 1993

[51] Int. Cl.$^5$ ................................................ C25F 3/16
[52] U.S. Cl. ............................ 204/129.1; 204/129.43
[58] Field of Search .............. 204/129.1, 129.4, 129.43

[56] References Cited

U.S. PATENT DOCUMENTS 3,657,083  4/1972  Larson ............................. 204/129.2

OTHER PUBLICATIONS

"Electrolytic Polishing", W. C. Elmore, J. Appl. Phys., vol. 10, Oct. 1939, pp. 724–727.
"Mechanism of Electropolishing", T. P. Hoar et al, Nature, vol. 165, 1950, pp. 64–65.
"The Anodic Behavior of Metals", T. P. Hoar, *Modern Aspects of Electrochemistry*, 2, Ed. J.O'M. Bockris, Academic Press, New York, 1959, pp. 262–342.
"The Mechanism of electrolytic Polishing", W. J. McG. Tegart, *The Electrolytic and Chemical Polishing of Metals in research and industry* (2nd Edition), 1959, pp. 1–12.
*Transmission Electron Microscopy of Metals*, G. Thomas, John Wiley & Sons, Inc., New York, 1962, pp. 150–157, FIG. 87.
"Automatic Unit for Thinning Transmission Electron Microscopy Specimens of Metals", R. D. Schoone and E. A. Fischione, Reprinted from The Review of Scientific Instruments, vol. 37, No. 10, Oct. 1966, pp. 1351–1353.
"Specimen preparation for electron metallography", I. S. Brammar et al, Blackwell Scientific, American Elsevier Publishing Co., New York, 1966, pp. 4, 5, 26–38.
"Controlled Jet Polishing of Specimens for Transmission Electron Microscopy", C. K. H. Dubose et al, Rev. Sci. Instr., 38, 1967, pp. 694–695.
"An Ellipsometric Study of Surface Films on Copper Electrodes Undergoing Electropolishing", M. Novak et al, J. Electrochem. Soc., vol. 117, No. 6, 1970, pp. 733–737.
"Solution-Side Transport Processes in the Electropolishing of Copper in Phosphoric Acid", K. Kojima et al, J. Electrochem. Soc., vol. 120, No. 8, 1973, pp. 1026–1033.
"Specimen Preparation in Materials Science", P. J. Goodhew, *Practical Methods in Electron Microscopy*, vol. 1, Ed. A. M. Clauert, North-Holland, 1973, pp. 48–77.
"The Influence of Specimen Thickness on X-ray Count Rates in STEM-Microanalysis", M. N. Thompson et al, Philosophical Magazine, vol. 35, No. 6, 1977, pp. 1537–1542.

(List continued on next page.)

*Primary Examiner*—Donald R. Valentine
*Attorney, Agent, or Firm*—Andrus, Sceales, Starke & Sawall

[57] ABSTRACT

A method is provided for microelectropolishing a transmission electron microscopy nonhomogeneous multi-element compound foil. The foil is electrolyzed at different polishing rates for different elements by rapidly cycling between different current densities. During a first portion of each cycle at a first voltage a first element electrolyzes at a higher current density than a second element such that the material of the first element leaves the anode foil at a faster rate than the second element and creates a solid surface film, and such that the solid surface film is removed at a faster rate than the first element leaves the anode foil. During a second portion of each cycle at a second voltage the second element electrolyzes at a higher current density than the first element, and the material of the second element leaves the anode foil at a faster rate than the first element and creates a solid surface film, and the solid surface film is removed at a slower rate than the second element leaves the foil. The solid surface film is built up during the second portion of the cycle, and removed during the first portion of the cycle.

10 Claims, 4 Drawing Sheets

OTHER PUBLICATIONS

"Limitations in the X-ray Microanalysis of Thin Foils in a Scanning Transmission Electron Microscope", P. Doig et al, Journal of Microscopy, vol. 110, Pt. 2, Jul. 1977, pp. 107–112.

*Electron Microscopy of Thin Crystals*, P. Hirsch et al, Robert E. Krieger Publishing Co., Malabar, Fla., 1965, 1977, pp. 24–39.

*Electron Microscope Specimen Preparation Techniques in Materials Science*, K. Thompson–Russell et al, Philips Technical Library, 1977, pp. 1–25.

"X–ray Microanalysis of Thin Foil Al–Ag Alloys", K. J. Sawley et al, J. Phys, D: Appl. Phys., vol. 10, 1977, pp. 1883–1889.

"Comment on X–ray Microanalysis of Thin Al–Ag Foils", P. L. Morris et al, J. Phys. D: Appl. Phys., vol. 11, 1978, pp. L73–L76.

"Photoeffects on the $Cu/H_3PO_4$ Interface", B. Pointu et al, J. Electroanal. Chem., 122 (1981), pp. 111–131.

"Diffusion and Solid–Film Formation during Electropolishing of Metals", R. Kirchheim et al, J. Electrochem. Soc., 128, 1981, pp. 1027–1034.

"A Microchemical Study of Surface Films on Aluminum Alloy Foils for AEM", P. J. Lee, *Analytical Electron Microscopy–1984*, D. B. Williams and D. C. Joy, Eds., San Francisco Press, 1984, pp. 69–72.

"The Automatic Twin–Jet Electropolisher" E. A. Fischione Instrument Manufacturing, 216 Red Oak Drive, Pittsburgh, Pa. 15239, 1990.

MULTI-ELEMENT MICROELECTROPOLISHING METHOD

This invention was made with U.S. Government support awarded by the Department of Energy (DOE), Grant No. DE-AC02-82ER40077. The U.S. Government has certain rights in this invention.

BACKGROUND AND SUMMARY

The invention relates to microelectropolishing techniques, and more particularly to a method for microelectropolishing a transmission electron microscopy nonhomogeneous multi-element compound foil.

Electropolishing may be broken down into two distinct processes, macroelectropolishing or smoothing wherein large scale asperities are removed, and microelectropolishing or brightening wherein smaller (less than 1 micron) irregularities are removed. In immersion or bath electropolishing, both processes take place. Macroelectropolishing occurs as anode material diffuses into the electrolyte from surface asperities due to the greater concentration gradient thereat. Macroelectropolishing is provided by a viscus fluid film at the interface of the anode and the electrolyte. Microelectropolishing occurs as a thin solid film is formed on the anode. In ideal microelectropolishing, the rate of film creation on the anode is the same as the rate of film removal into the electrolyte, thus providing a thin stable film. In jet type electropolishing, the viscous layer usually cannot be maintained, and the dominant process is microelectropolishing. The material is polished, i.e. anode material is removed, until the anode foil is thin enough for transmission electron microscopy.

The present invention provides a method for microelectropolishing a transmission electron microscopy nonhomogeneous multi-element compound foil having different elements which polish at different rates.

DETAILED DESCRIPTION

Figure 1:
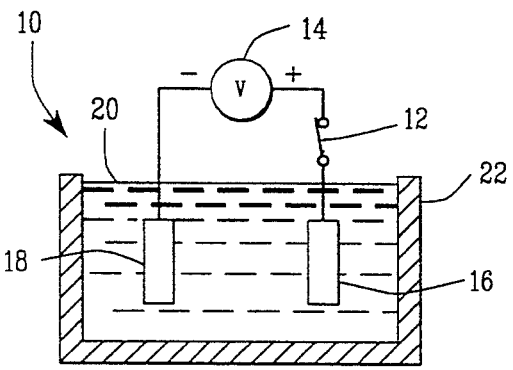
FIG. 1 schematically shows a polishing arrangement.
Figure 2:
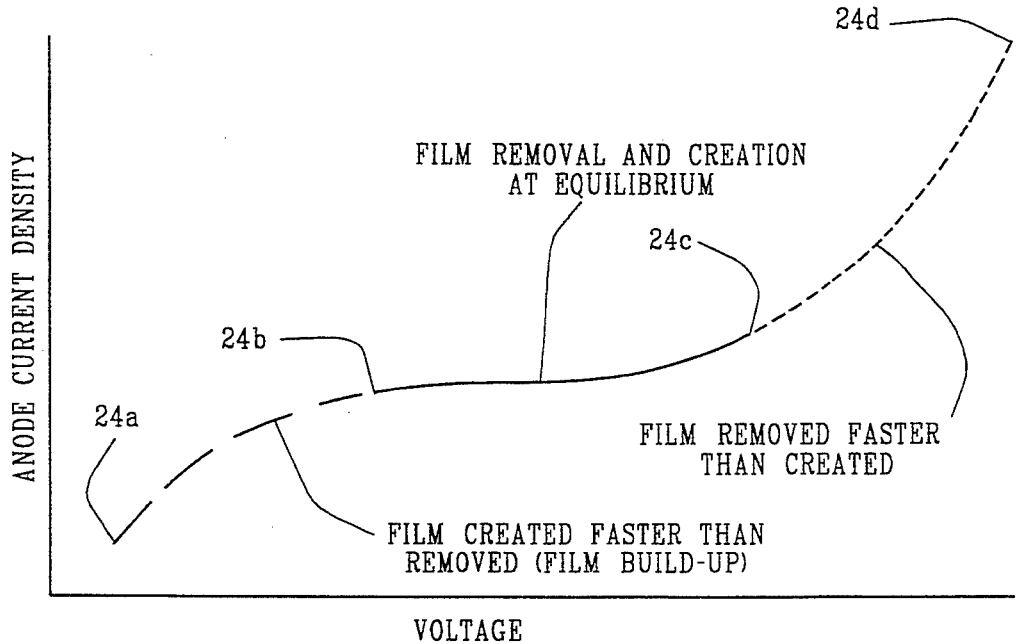
FIG. 2 is a graph of anode current density versus voltage.

FIG. 1 shows a typical electropolishing arrangement 10, like that shown in: *Transmission Electron Microscopy of Metals*, G. Thomas, John Wiley & Sons, Inc., New York, 1962, pp. 150–157, FIG. 87; *Electron Microscopy of Thin Crystals*, P. Hirsch et al, Robert E. Krieger Publishing Co., Malabar, Fla., 1965, 1977, pp. 24–39, FIG. 2.3; and *Electron Microscope Specimen Preparation Techniques in Materials Science*, K. Thompson-Russell et al, Philips Technical Library, pp. 1–25, FIG. 5(b). Closure of switch 12 completes a circuit from voltage source 14 such that current flows from positive anode 16 to negative cathode 18 through electrolyte 20 in tank 22. FIG. 2 shows at curve 24 a plot of anode current density versus voltage, and is like FIG. 88 in the above noted Thomas reference, and FIG. 2.1 in the above noted Hirsch et al reference, and FIG. 5(a) in the above noted Thompson-Russell reference. As the anode potential increases, the current density initially increases, followed by a plateau, followed by a further increase of current density. During the dashed-line portion of curve 24 from point 24a to point 24b, material leaves the anode and forms a film on the anode surface at a faster rate than such film is removed into the electrolyte, i.e. a film is built-up on the anode surface. The solid-line portion between points 24b and 24c is the plateau where polishing occurs and is where film removal and creation are at equilibrium. During the dotted-line portion of curve 24 between point 24c and point 24d, the film is removed into the electrolyte at a faster rate than it is created on the surface of the anode. Conventional bath-type electropolishing is carried out on the plateau between points 24b and 24c.

Figure 3:
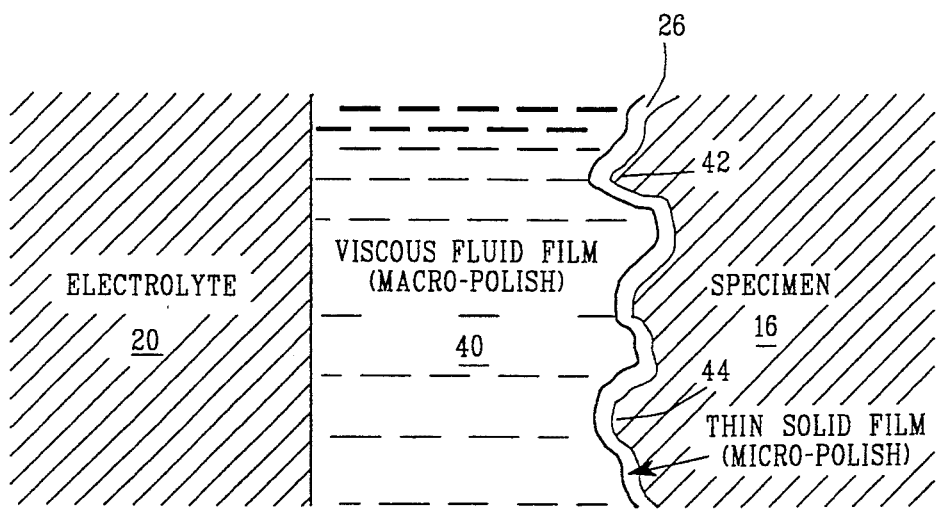
FIG. 3 is an enlarged view of anode interface conditions.

FIG. 3 is like FIG. 2.2 in the Hirsch et al reference. As noted in Hirsch et al, page 26, the various stages of curve 24, FIG. 2, can be associated with the formation of surface films on anode 16, FIGS. 1 and 3. At the start of the curve, a thin (10–100 angstroms) solid surface film 26, FIG. 3, is formed on the anode, and is maintained through point 24d of curve 24. The film is usually an oxide and is similar to that formed during passivation of a surface and is responsible for the micropolish or brilliance of the surface. During polishing, the film is continually being dissolved and reformed, i.e. alternate oxidation and passivation. A second surface film 40 is formed at point 24b of curve 24, which film is a viscous fluid film and is responsible for macropolishing. The diffusion rate of anode material across viscous layer 40 is great from surface asperities such as 42 and 44 due to the greater concentration gradient thereat, and thus the asperities are removed faster, and macroelectropolishing occurs. In order for microelectropolishing (sometimes called brightening or brilliance) to occur, material should be removed from the anode surface irrespective of features such as grain boundaries, grain orientation, and defects. In ideal microelectropolishing, the rate of removal of film 26 at the interface thereof with viscous film 40 is equal to the rate of creation of film 26 on the surface of anode 16.

Figure 4:
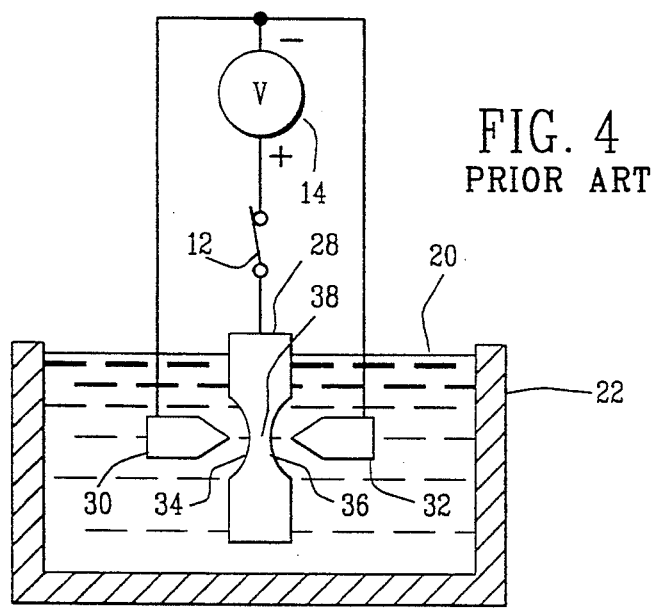
FIG. 4 shows a further embodiment of FIG. 1.

The noted plateau between point 24b and point 24c of curve 24 is present only if the cathode area is large compared with the anode area. FIG. 4 shows an embodiment where such plateau is not observed, and is like FIGS. 89 and 90 of the Thomas reference, and FIGS. 2.10 and 2.11 of the Hirsch et al reference. In FIG. 4, anode 28 is provided between point cathodes 30 and 32 which provide more localized polishing, yielding dished-out regions 34 and 36 and thin region 38 therebetween. Anode 28 is polished until thin region 38 just begins to perforate, to provide a transmission electron microscopy foil. The sample is polished by applying a voltage at which film removal and creation are at equilibrium.

Figure 5:
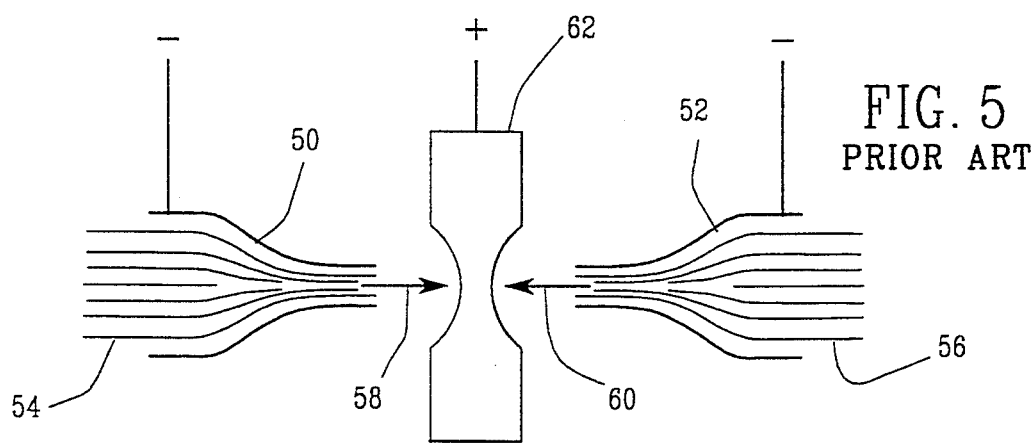
FIG. 5 shows another polishing arrangement.
Figure 6:
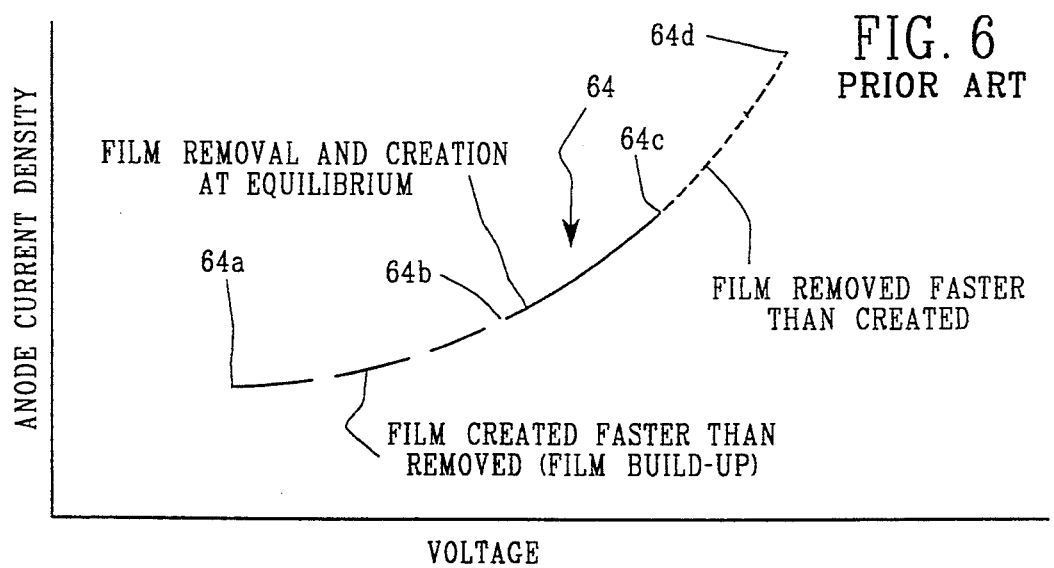
FIGS. 6–9 are graphs of anode current density versus voltage.
Figure 7:
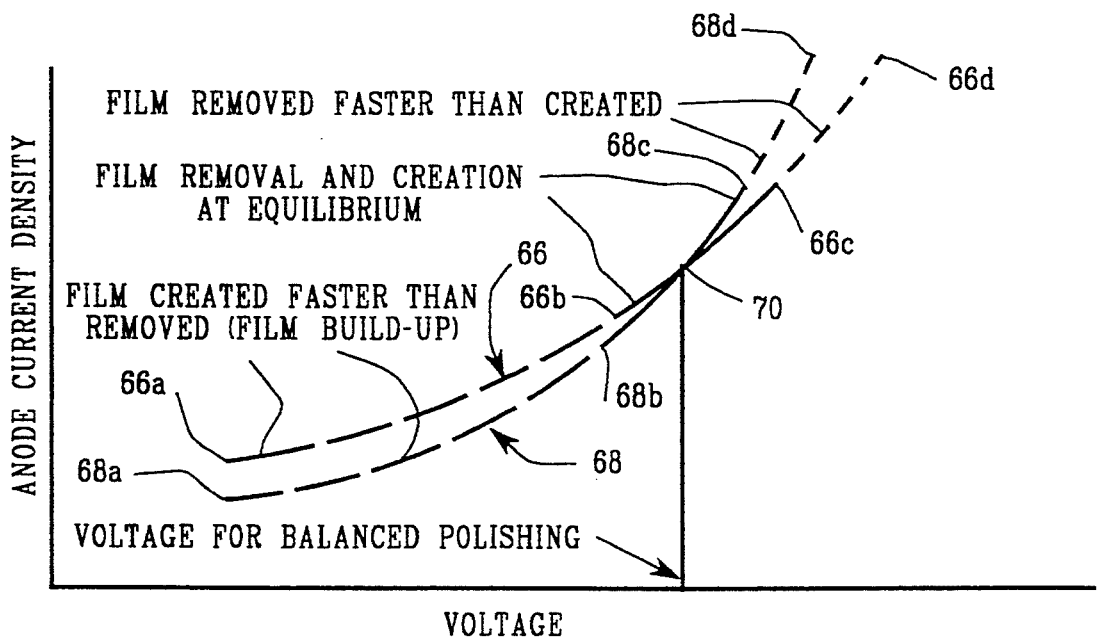
Figure 8:
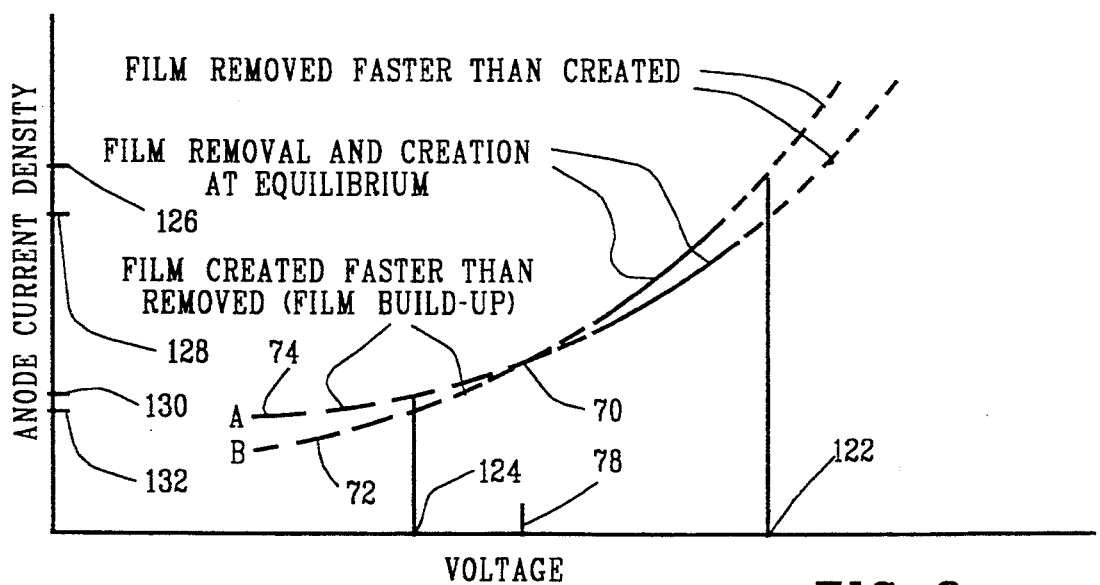
Figure 9:
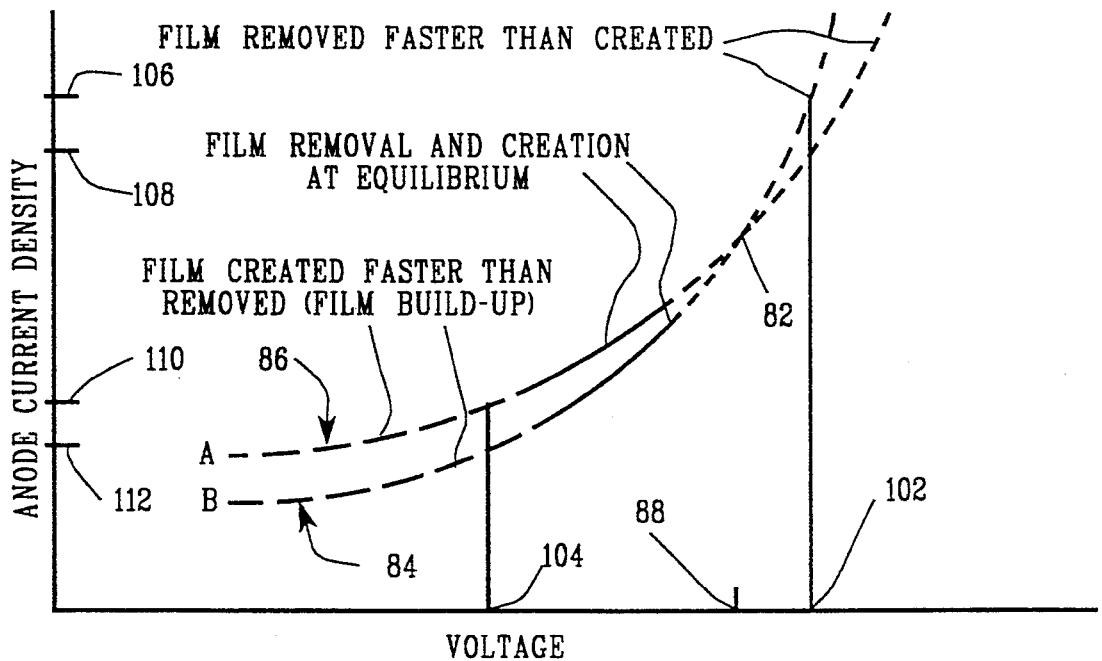

FIG. 5 schematically illustrates jet electropolishing, and is like FIG. 2.13 of the Hirsch et al reference, and FIGS. 7–9 of the Thompson-Russell reference. Jet electropolishers are commercially available from E.A. Fischione Instrument Manufacturing, 216 Red Oak Drive, Pittsburgh, Pa. 15239. Nozzles 50 and 52 direct negatively charged electrolyte 54 and 56 at jets or streams 58 and 60 against anode 62. The electrolyte is forced onto the specimen surface in a tightly focused jet (typically about 1.5 millimeters in diameter) to produce selective area polishing. Under these conditions, the viscous layer 40, FIG. 3, usually cannot be maintained, and the dominant process is microelectropolishing. The resulting relationship between current and voltage is shown in FIG. 6 at curve 64, which is like FIG. 10 of the Thompson-Russell reference. During the dashed-line portion of the curve from point 64a to point 64b, film 26, FIG. 3, is created faster than it is removed. The optimum polishing conditions occur during the solid-line portion of the curve from point 64b to point 64c where the film is removed at about the same rate as it is created, i.e. film removal and creation are at equilibrium. During the dotted-line portion of the curve from point 64c to point 64d the film is removed faster than it is created.

The anode current density versus voltage curves vary according to the material of anode 16. Electropolishing rates and ideal polishing conditions are different for different elements. For a compound material having two or more elements, each element will have its own characteristic current versus voltage curve. In microelectropolishing such multi-element materials, a compromise or trade-off must be made between the differing characteristics. The tight balance of conditions often means that great care must be taken in creating stable and controlled electropolishing conditions. In multi-element materials, it can be difficult if not impossible to find a single polishing condition in which all elements or phases are polished acceptably and at a similar rate. FIG. 7 shows an example where this balance can be attained.

In the example illustrated in FIG. 7, the anode includes a first element having a polishing curve 66, and a second element having a polishing curve 68. During the dashed-line portion of curve 66 between point 66a and point 66b, film creation for the first element or phase is faster than film removal for the first element. During the solid-line portion of curve 66 between point 66b and point 66c, film removal and creation for the first element are at equilibrium. During the dotted-line portion of curve 66 between point 66c and point 66d, film removal for the first element is faster than film creation for the first element. During the dashed-line portion of curve 68 between point 68a and point 68b, film creation for the second element or phase is faster than film removal for the second element. During the solid-line portion of curve 68 between point 68b and point 68c, film removal and creation for the second element are at equilibrium. During the dotted-line portion of curve 68 between point 68c and point 68d, film removal for the second element is faster than film creation for the second element. Because the solid-line portions of curves 66 and 68 cross over, at cross-over point 70, both elements or phases can be polished. In this circumstance, only one voltage-current condition is required for a uniform polish. The more phases or elements in the sample, the less likely that this situation is available.

FIG. 8 shows a two element or phase electropolishing example where the current-voltage curves 72 and 74 for different materials have a cross-over point 76 outside of the solid-line equilibrium portions of the curves, namely where such cross-over point is below the solid-line equilibrium portion of one or more of the curves. Thus, applying voltage 78 in FIG. 8 provides equal polishing as between the different elements, i.e. equal anode current densities, however each element is in the film build-up dashed-line portion of its respective curve 72 and 74, and hence the polishing is not optimum.

FIG. 9 illustrates the situation where the cross-over point 82 of curves 84 and 86 of first and second different elements occurs in the dotted-line film removal region above the solid-line equilibrium regions. Thus, applying voltage 88 in FIG. 9 removes the first and second elements at equal rates, i.e. the anode current density is the same for each, however the film is not balanced by an equal rate of creation.

In the present invention, the anode foil is electrolyzed at a first voltage 102, FIG. 9, providing faster polishing of the first element of curve 84 than the second element of curve 86, and then electrolyzed at a second voltage 104 providing faster polishing of the second element of curve 86 than the first element of curve 84, and alternately and repetitively electrolyzing the anode foil at the upper and lower voltages 102 and 104 for respective first and second time intervals over a plurality of cycles. Additional voltage levels are included in the cycle as needed for additional elements of a multi-element compound anode foil.

As seen at voltage 102, FIG. 9, the first element at curve 84 electrolyzes at current density 106 which is greater than current density 108 at which the second element electrolyzes at curve 86. At the lower voltage 104, the second element at curve 86 electrolyzes at current density 110 which is greater than the current density 112 at which the first element electrolyzes at curve 84. During a first portion of each cycle as provided at voltage 102, the material of the first element, curve 84, leaves the anode foil at a faster rate at current density 106 than the second element at current density 108, and creates a solid surface film 26, FIG. 3. Also during this first portion of the cycle, at voltage 102, the solid surface film is removed into the electrolyte at a faster rate than the first element leaves the anode foil, i.e. the film is removed faster than it is created. During a second portion of each cycle, as provided at voltage 104, the material of the second element, curve 86, leaves the anode foil at a faster rate at current density 110 than the first element at current density 112, and creates a solid surface film 26. During this second portion of the cycle, at voltage 104, the solid surface film is removed at a slower rate than the second element leaves the anode foil, i.e. the film is created faster than it is removed. In this manner, the solid surface film is built up during the second portion of the cycle at voltage 104, and removed during the first portion of the cycle at voltage 102. It is preferred that the microelectropolishing be both started and stopped during the noted first portion of the cycle at the higher voltage 102, rather than during the second portion of the cycle at the lower voltage 104, to minimize excess film build-up. If more than two elements and/or voltages are used, it is preferred that the microelectropolishing be started and stopped at the highest voltage during the cycle.

As seen in FIG. 9, the first element, curve 84, polishes at a first rate of current density versus voltage, and the second element, curve 86, polishes at a second rate of current density versus voltage, which rates define the slope curves 84 and 86, which curves cross at cross-over point 82. The anode foil is electrolyzed at upper voltage 102 providing faster polishing of the first element than the second element, and is then electrolyzed at the lower voltage 104 providing faster polishing of the second element than the first element. Upper voltage 102 is greater than cross-over voltage 88, and lower voltage 104 is less than cross-over voltage 88. The slope of curve 84 is steeper than the slope of curve 86. At upper voltage 102, current density 106 for the first element, corresponding to material of the first element leaving the anode foil, is greater than current density 108 for the second element, corresponding to material of the second element leaving the anode foil. Hence, at upper voltage 102, the material of the first element leaves the anode foil at a faster rate than the material of the second element leaves the anode foil. At lower voltage 104, current density 110 for the second element, corresponding to material of the second element leaving the anode foil, is greater than current density 112 for the first element, corresponding to material of the first element leaving the anode foil. Hence, at lower voltage 104, the material of the second element leaves the anode foil at a faster rate than the material of the first element leaves the anode foil.

The anode foil is electrolyzed at different polishing rates for different elements, including at least a first element having an equilibrium current density and voltage, as shown at the solid-line portion of curve 84 in FIG. 9, wherein the material of the first element leaves the anode foil to form a solid surface film and the material of the solid surface film is removed into electrolyte at a rate equal to the rate of the first element leaving the anode foil to create the solid surface film, and including at least a second element having an equilibrium current density and voltage, as shown at the solid-line portion of curve 86 in FIG. 9, wherein the material of the second element leaves the anode foil to form a solid surface film, and the material of the solid surface film is removed into electrolyte at a rate equal to the rate of the second element leaving the anode foil to create the solid surface film. The anode foil is electrolyzed at a first voltage 102 providing faster polishing of the first element at current density 106 than the second element at current density 108, and then is electrolyzed at a second voltage 104 providing faster polishing of the second element at current density 110 than the first element at current density 112. Current density 106 is greater than the equilibrium current density of the first element at the solid-line portion of curve 84. Current density 110 is less than the equilibrium current density of the second element at the solid-line portion of curve 86.

The invention is also applicable where the cross-over point 76, FIG. 8, is below the equilibrium current density of one or both of the elements or phases as shown at the solid-line portions of curves 72 and 74. The anode foil is electrolyzed at upper voltage 122 providing faster polishing of the first element, curve 72, than the second element, curve 74, and the anode foil is then electrolyzed at at least a second lower voltage 124 providing faster polishing of the second element, curve 74, than the first element, curve 72. At upper voltage 122, the first element at curve 72 electrolyzes at current density 126 which is greater than the current density 128 at which the material of the second element electrolyzes at curve 74. At the lower voltage 124, the second element at curve 74 electrolyzes at current density 130 which is greater than the current density 132 at which the first element electrolyzes at curve 72. Voltage 122 is greater than cross-over voltage 78, and voltage 124 is less than cross-over voltage 78. Voltage 122 is also greater than the equilibrium voltage of one or both of the elements as shown at the solid-line portions of curves 72 and 74. Lower voltage 124 is less than one or both of the equilibrium voltages.

In FIG. 7, the cross-over point 70 in the removal rates of the two elements or phases, curves 66 and 68, occurs under conditions where both elements are being polished, i.e. film removal and creation at equilibrium. In these circumstances, only one voltage-current condition is required for a uniform polish. As noted above, the more elements or phases in the sample, the less likely that this situation will occur. FIG. 7 thus shows ideal two-phase electropolishing wherein film build-up is balanced by film removal.

In FIG. 8, the cross-over point 76 in the removal rates of the two elements or phases, curves 72 and 74, occurs under conditions where one or both elements are in the film build-up condition. By cycling between lower voltage 124 in the film build-up condition, where the second element, curve 74, is being removed faster than the first element, curve 72, and upper voltage 122 where the film is removed faster than it is created where the first element, curve 72, is being removed faster than the second element, curve 74, a polishing condition can be established where both elements are being removed at the same rate. In this manner, two-phase electropolishing conditions can be accommodated where the cross-over in polishing rates occurs in the film build-up region.

In FIG. 9, the equilibrium cross-over point 82 in the removal rates of the two elements or phases, curves 84 and 86, occurs under conditions where one or both elements are in the film removal region, i.e. the film removal rate is faster than the rate of film formation. By cycling between lower voltage 104 in the film build-up condition where the second element, curve 86, is being removed faster than the first element, curve 84, and the upper voltage 102 where the film is removed faster than it is created where the first element, curve 84, is being removed faster than the second element, curve 86, a polishing condition can be established where both elements or phases are being removed at the same rate. In this manner, two-phase electropolishing conditions can be accommodated where the cross-over in polishing rates occurs under conditions where there is otherwise faster film removal than build-up.

Figure 10:
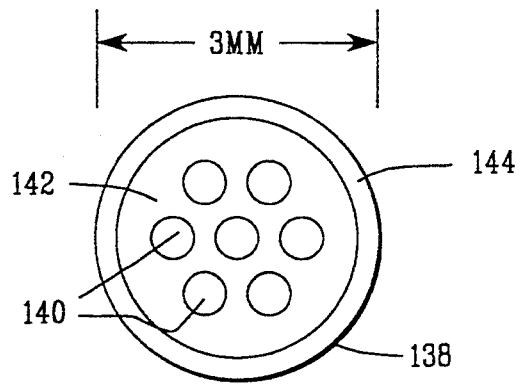
FIG. 10 is a schematic view of a specimen.

In one implementation involving niobium titanium strands in a copper wire which is copper plated to a wire diameter of 3 millimeters, the wire is transversely sliced to a thickness of about 60 microns, to provide a disc or foil 138 as shown in FIG. 10 having a diameter of about 3 millimeters, and a thickness (into the page) of about 60 microns, wherein the niobium titanium strands are shown at 140, the copper wire at 142, and the copper plating at 144. Disc or foil 138 was used as anode 62 in the jet polishing arrangement of FIG. 5. The electrolytic solution was 2% by volume HF, 5% by volume $H_2SO_4$, and 93% by volume methanol at a temperature of $-40°$ C. An initial voltage of 140 volts providing a current density of 25 milliamps per square millimeter was applied for 2 seconds, followed by oscillation between 140 volts providing 25 milliamps per square millimeter for 200 milliseconds, and 70 volts providing 12 milliamps per square millimeter for 100 milliseconds, thus providing a cycle of 300 milliseconds. The cycle is continuously repeated until the specimen just begins to perforate, usually in about 3 to 6 minutes. The initial 2 second high current density interval is desired for cleaning the surface. In another implementation involving $Nb_3Sn$ and bronze, an initial 2 second interval at 200 volts providing 35 milliamps per square millimeter is followed by a plurality of cycles each having a first portion at 200 volts providing 35 milliamps per square millimeter for 40 milliseconds followed by a second portion at 35 volts providing 6 milliamps per square millimeter for 90 milliseconds.

It is recognized that various equivalents, alternatives and modifications are possible within the scope of the appended claims.

I claim:

1. A method for microelectropolishing a transmission electron microscopy nonhomogeneous multi-element compound foil, comprising electrolyzing said foil at a first voltage providing faster polishing of a first element of said foil than a second element of said foil, and electrolyzing said foil at at least a second voltage providing faster polishing of said second element than said first element.

2. The method according to claim 1 comprising alternately and repetitively electrolyzing said foil at at least said first and second voltages for respective first and second time intervals over a plurality of cycles,
   such that during a first portion of each cycle at said first voltage said first element electrolyzes at a higher current density than said second element, and the material of said first element leaves said foil at a faster rate than said second element and creates a solid surface film, and such that the solid surface film is removed at a faster rate than said first element leaves said foil,
   and such that during a second portion of each cycle at said second voltage said second element electrolyzes at a higher current density than said first element, and the material of said second element leaves said foil at a faster rate than said first element and creates a solid surface film, and such that the solid surface film is removed at a slower rate than said second element leaves said foil,
   such that a solid surface film is built-up during said second portion of said cycle, and removed during said first portion of said cycle.

3. The method according to claim 2 comprising stopping said microelectropolishing during said first portion of said cycle at said first voltage, rather than during said second portion of said cycle at said second voltage.

4. A method for microelectropolishing a transmission electron microscopy nonhomogeneous multi-element compound foil, comprising electrolyzing said foil at different polishing rates for different elements, wherein at least a first element of said foil polishes at a first rate of current density versus voltage, and a second element of said foil polishes at a second rate of current density versus voltage, which rates define slope curves in a plot of current density versus voltage, which slope curves cross at a cross-over point at a cross-over voltage, and comprising electrolyzing said foil at a first voltage providing faster polishing of said first element than said second element, and electrolyzing said foil at a second voltage providing faster polishing of said second element than said first element, said first voltage being greater than the cross-over voltage, and said second voltage being lower than the cross-over voltage.

5. The method according to claim 4 wherein the ratio of current density to voltage for said first element has a first slope, and the ratio of current density to voltage for said second element has a second slope,
   such that at said first voltage, current density for said first element, corresponding to material of said first element leaving said foil, is greater than current density for said second element, corresponding to material of said second element leaving said foil, such that the material of said first element leaves said foil at a faster rate than the material of said second element leaves said foil,
   and such that at said second voltage, current density for said second element, corresponding to material of said second element leaving said foil, is greater than current density for said first element, corresponding to material of said first element leaving said foil, such that the material of said second element leaves said foil at a faster rate than the material of said first element leaves said foil.

6. A method for microelectropolishing a transmission electron microscopy nonhomogeneous multi-element compound foil, comprising electrolyzing said foil at different polishing rates for different elements, wherein
   at least a first element of said foil has an equilibrium current density and voltage wherein the material of said first element leaves said foil to form a solid surface film, and the material of the solid surface film is removed into electrolyte at a rate equal to the rate of said first element leaving said foil to create a solid surface film,
   and at least a second element as an equilibrium current density and voltage wherein the material of said second element leaves said foil to form a solid surface film, and the material of the solid surface film is removed into electrolyte at a rate equal to the rate of said second element leaving said foil to create the solid surface film,
   and comprising electrolyzing said foil at a first current density providing faster polishing of said first element than said second element, and electrolyzing said foil at at least a second current density providing faster polishing of said second element than said first element, said first current density being greater than said equilibrium current density of said first element, said second current density being less than said equilibrium current density of said second element.

7. The method according to claim 6 wherein said first current density is greater than said equilibrium current density of said second element.

8. The method according to claim 6 wherein said second current density is less than said equilibrium current density of said first element.

9. The method according to claim 6 wherein said first current density is greater than the equilibrium current density of each of said first and second elements, and said second current density is less than the said equilibrium current density of each of said first and second elements.

10. The method according to claim 6 wherein said equilibrium current density of said first element is greater than said equilibrium current density of said second element, said first current density is greater than said equilibrium current density of each of said first and second elements, and said current density is less than said equilibrium current density of each of said first and second elements.

* * * * *